(12) United States Patent
Ateshian et al.

(10) Patent No.: US 6,459,948 B1
(45) Date of Patent: Oct. 1, 2002

(54) ANATOMICALLY CORRECT PROSTHESIS AND METHOD AND APPARATUS FOR MANUFACTURING PROSTHESIS

(75) Inventors: Gerard A. Ateshian, New York; Van C. Mow, Briarcliff Manor, both of NY (US); Robert J. Pawluk, Montvale, NJ (US); Melvin P. Rosenwasser, Palisades, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/414,939

(22) Filed: Oct. 8, 1999

Related U.S. Application Data

(63) Continuation of application No. 08/674,826, filed on Jul. 3, 1996, now Pat. No. 6,126,690.

(51) Int. Cl.$^7$ .............................................. G06F 19/00
(52) U.S. Cl. .................... 700/117; 623/11.11; 623/21.11
(58) Field of Search ................................ 700/117, 159; 128/916, 922, 923; 623/11.11, 16.11, 18.11, 22.11

(56) References Cited

U.S. PATENT DOCUMENTS

| | | |
|---|---|---|
| 4,231,121 A | 11/1980 | Lewis |
| 4,242,759 A | 1/1981 | White |
| 4,276,660 A | 7/1981 | Laure |
| 4,304,011 A | 12/1981 | Whelan, III |
| 4,352,212 A | 10/1982 | Greene et al. |
| 4,436,684 A | 3/1984 | White |
| 4,642,122 A | 2/1987 | Steffee |
| 4,662,888 A | 5/1987 | Field |
| 4,685,919 A | 8/1987 | Niwa et al. |
| 4,704,686 A | 11/1987 | Aldinger |
| 4,725,280 A | 2/1988 | Laure |
| 4,731,087 A | 3/1988 | Sculco et al. |
| 4,784,661 A | 11/1988 | Beckenbaugh |
| 4,822,365 A | * 4/1989 | Walker et al. ................. 623/20 |
| 4,936,860 A | 6/1990 | Swanson |
| 4,936,862 A | * 6/1990 | Walker et al. ................. 623/23 |
| 4,955,916 A | 9/1990 | Carignan |
| 4,969,908 A | 11/1990 | Swanson |
| 5,007,932 A | 4/1991 | Bekki et al. |
| 5,037,440 A | 8/1991 | Kowning |
| 5,047,059 A | 9/1991 | Saffar |
| 5,147,386 A | 9/1992 | Carignan et al. |
| 5,150,304 A | 9/1992 | Berchem et al. |
| 5,201,766 A | 4/1993 | Georgette |
| 5,326,364 A | 7/1994 | Clift, Jr. |
| 5,360,446 A | * 11/1994 | Kennedy ....................... 623/16 |
| 5,405,404 A | 4/1995 | Linscheid |

(List continued on next page.)

OTHER PUBLICATIONS

Patient Matched Implants catalog, Biomet, Inc. "Customized Hip Prosthesis", New Scandinavian Technology.

"Quantitation Of Articular Surface Topography And Cartilage Thickness In Knee Joints Using Sterophotogrammetry", Ateshian, et al., J. Biomechanics, vol. 24, No. 8, pp. 761–776, 1996.

"Curvature Characteristics And Congruence Of The Thumb Carpometacarpal Joint: Difference Between Female and Male Joints" Ateshian, et al., J. Biomechanics, vol. 25, No. 6, pp. 591–607, 1992.

*Primary Examiner*—Thomas Black
*Assistant Examiner*—Ronald D Hartman, Jr.
(74) *Attorney, Agent, or Firm*—John P. White; Cooper & Dunham LLP (57) ABSTRACT

A joint prosthesis for attachment to a bone of a patient, comprising an anchor with a head surface and a stem for attachment to an end of the bone, the head surface having an anatomically accurate shape.

31 Claims, 5 Drawing Sheets

U.S. PATENT DOCUMENTS

| | | |
|---|---|---|
| 5,507,821 A | 4/1996 | Senwald |
| 5,507,822 A | 4/1996 | Bouchon |
| 5,549,690 A | 8/1996 | Hollister |
| 5,645,605 A | 7/1997 | Klawitter |
| 5,702,469 A | 12/1997 | Whipple |
| 5,769,092 A * | 6/1998 | Williamson, Jr. ............ 128/898 |
| 5,824,085 A * | 10/1998 | Sahay et al. ................... 623/16 |
| 6,126,690 A * | 10/2000 | Ateshian et al. ............... 623/18 |
| 6,241,775 B1 * | 6/2001 | Blatchford ................... 623/27 |

* cited by examiner

ANATOMICALLY CORRECT PROSTHESIS AND METHOD AND APPARATUS FOR MANUFACTURING PROSTHESIS

This is a continuation of application Ser. No. 08/674,826 filed Jul. 3, 1996, now U.S. Pat. No. 6,126,690.

BACKGROUND OF THE INVENTION

The present invention relates to a joint prosthesis and method of producing same.

Within this application several publications are referenced by arabic numerals within parenthesis. Full citations for these references may be found at the end of the specification immediately preceding the claims. The disclosures of all of these publications in their entireties are hereby incorporated by reference into this application in order to more fully describe the state of the art to which this invention pertains.

Various joint prostheses have been designed and produced, such as the Swanson trapezial implant, the Swanson condylar implant, the De la Caffiniere prosthesis, the Braun design, the Kessler design, the Mayo clinic prosthesis, the Helal spacer, the Eaton trapezial implant, and the Niebauer "tie-in" design.

In addition, various patents have been granted on joint prostheses and methods of making them. For example, U.S. Pat. No. 4,704,686 to Aldinger ("Aldinger") relates to the fabrication of bone replacement prosthesis using tomography. Specifically, tomographic pictures of cross-sections of the bone are taken to determine characteristics of the bone, such as the locations of different bone densities. This data is then used to calculate the size and placement of a series of disks which when connected form the desired prosthesis shape. The prosthesis is machined according to these calculations. The use of bone cement is minimized or eliminated because the accurate shape of the resulting prosthesis leaves little space between the prosthesis and the remaining bone.

Although Aldinger discusses the custom fabrication of prostheses based on the shape and density of the patient's bone so that a prosthesis can be press-fit into the bone, the patent does not teach the use of imaging data to custom fabricate anatomic articular surfaces for the joint itself. In this regard it is noted that as used herein the terms "anatomic" and "anatomically accurate" may relate to shapes that are either calculated or stored in a database. Moreover, it is noted that the term "spline surfaces" is a general term that includes both biquintic and B-spline surfaces, for example.

In U.S. Pat. No. 5,037,440 to Koenig ("Koenig"), each anchor stem of a prosthesis is press-fit into a hole created in the bone on a respective side of the joint. One anchor has a complex convex surface which wraps around the end of the bone and the other anchor has a complex concave surface. The only contact between the anchors, which are not attached, are the complex surfaces which can slide against each other. The surfaces are not, however, anatomically correct.

U.S. Pat. No. 4,725,280 to Laure ("Laure '280") shows a saddle-like finger joint prosthesis having a "V"-shaped tab anchor and a valley-shaped slot anchor. Specifically, the "V"-shaped tab anchor has concave sides and the slot anchor has convex sides. Since the tab anchor slides along the bottom of the valley of the slot anchor, undesired sideward movement of the joint is restricted. While the two anchors are not attached to each other, the prosthesis does not provide for two anatomically correct contact and load-bearing surfaces.

U.S. Pat. No. 4,276,660 to Laure ("Laure '660") relates to a thumb joint prosthesis that utilizes a ball and socket configuration. Again, this patent does not teach anatomically correct contact and load-bearing surfaces.

U.S. Pat. No. 5,150,304 to Berchem et al. ("Berchem et al.") relates to a method of fabricating an implantable joint prosthesis. Specifically, a computer determines the shape of the joint prosthesis before surgery from computations, such as finite element analysis, so that undercuts can be eliminated and so that the stress is uniformly distributed. The computations are based on data received from imaging scans of the patient's bone. Once the shape of the bone is determined the prosthesis is either selected from a collection of prostheses or machined using computer-aided manufacturing.

While the Berchem et al. patent discusses the use of a mathematical model for making a joint implant prosthesis based on imaging results of the patient's bone, there is no teaching to use mathematically described anatomic joint surfaces derived from the examination of other joints to create the prosthesis. Furthermore, unlike the anatomically correct joint surfaces of the subject invention, the non-articular surface is tailored to reduce stress and not to recreate a healthy articular joint surface.

U.S. Pat. No. 4,436,684 to White ("White") relates to a method of forming implantable prosthesis for reconstructive surgery. A selected internal skeletal structure is measured by subjecting the body to radiant energy to produce radiant energy responses that are detected to obtain representations delineating the skeletal structure. Three dimensional coordinate data defining the skeletal structure is generated from the obtained representations. The coordinate data is employed to control a sculpting tool to form the prosthesis.

While the White patent discusses the use of radiant energy to obtain skeletal structure information utilized to fabricate a prosthesis, there is no teaching to use mathematically described anatomic joint surfaces, or archetypes, derived from the examination of other joints to create the prosthesis.

SUMMARY OF THE INVENTION

Accordingly, it is an object of the present invention to provide a joint prosthesis in which the relative motion of the two components of the joint is provided by sliding motion between two anatomically accurate surfaces.

It is a further object of the present invention to provide a joint prosthesis in which the motion of the joint is physiologic because the contacting articular surfaces are anatomic in shape and highly accurate in topography.

It is a further object of the present invention to provide a joint prosthesis in which constraints that result from the articular surface shapes at their extremes of motion contribute to reducing stress in capsular tissues, as occurs in physiologic conditions.

It is a further object of the present invention to provide a joint prosthesis in which loosening of the prosthesis can not result from distraction of the joint because the articular contacting surfaces are not attached.

It is a further object of the present invention to provide a joint prosthesis in which load transmission across the joint mimics physiologic conditions due to the highly accurate shape of the articular contacting surfaces.

It is a further object of the present invention to provide a joint prosthesis in which the geometry of the contact surfaces is described using spline surfaces which will reproduce highly accurately the shape of physiologic contact surfaces.

It is a further object of the present invention to provide a joint prosthesis in which both components of the joint prosthesis are press fit into respective bones of the joint.

It is a further object of the present invention to provide a joint prosthesis in which the surfaces of the joint prosthesis which come into contact with bone may be shaped and/or coated to promote an intimate bone/prosthesis interface bond and to promote functional stress transfer.

According to one aspect of the present invention, a joint prosthesis for attachment to a bone of a patient is provided, comprising an anchor with a head surface and a stem for attachment to an end of the bone, the head surface having an anatomically accurate shape.

According to another aspect of the present invention, a total joint prosthesis for attachment to two bones of a patient is provided, comprising two unjoined anchors, each with a head surface and a stem for attachment to ends of respective ones of the two bones, each of the head surfaces having an anatomically accurate shape.

According to another aspect of the present invention, a total joint prosthesis for attachment in the bones of a patient is provided, comprising two unjoined anchors, each with a head surface and a stem for attachment to end of respective ones of the two bones, each of the head surfaces having an anatomically accurate shape based upon a particular one of a plurality of articular joint surfaces within a database of mathematical descriptions of said plurality of articular joint surfaces.

According to another aspect of the present invention a method of manufacturing a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes to determine which one of the plurality of articular joint surface archetypes exhibits the smallest deviation in overall dimensions from the imaged data, and fabricating the joint prosthesis to resemble the articular joint surface archetype which exhibits the smallest deviation in overall dimensions from the imaged data.

According to another aspect of the present invention a method of selecting, from a collection, a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes to determine which one of the plurality of articular joint surface archetypes exhibits the smallest deviation in overall dimensions from the imaged data, and selecting, from the collection, the joint prosthesis which exhibits the smallest deviation in overall dimensions from the articular joint surface archetype which exhibits the smallest deviation in overall dimensions from the imaged data.

According to another aspect of the present invention a method of manufacturing a joint prosthesis for a patient with a healthy contralateral joint is provided, comprising obtaining imaging data of the patient's healthy contralateral joint surfaces, fabricating a mirror image replicate of the patient's imaged healthy contralateral joint surfaces.

According to another aspect of the present invention a method of manufacturing a joint prosthesis for a patient's bone is provided, comprising measuring a plurality of parameters including dimensions of the bone, the patient's weight, the patient's sex, and the patient's height, comparing the plurality of measured parameters with a respective plurality of corresponding parameters in a database of mathematical descriptions of a plurality of articular joint surface archetypes to determine which one of the plurality of articular joint surface archetypes has parameters exhibiting the most similarity to the measured parameters, and fabricating the joint prosthesis to resemble the articular joint surface archetype which has parameters exhibiting the most similarity to the measured parameters.

According to another aspect of the present invention a method of manufacturing a joint prosthesis for a patient's bone is provided, comprising obtaining imaging data of the joint surface of the patient's bone, modifying the imaged data of the joint surface of the patient's bone to provide a more functional surface topography, fabricating a replicate of the modified imaged data to provide a functional joint prosthesis.

According to another aspect of the present invention a method of manufacturing a joint prosthesis for a patient's bone is provided, comprising obtaining imaging data of the joint surface of the patient's bone, comparing the imaged data of the joint surface of the patient's bone with a database of mathematical descriptions of a plurality of articular joint surface archetypes, modifying the imaged data of the joint surface of the patient's bone to provide a more functional surface topography while exhibiting the smallest deviation in overall dimensions from one of the plurality of articular joint surface archetypes, fabricating the joint prosthesis to resemble the articular joint surface archetype which exhibits the smallest deviation in overall dimensions from the modified imaged data.

According to another aspect of the present invention a method of manufacturing a joint prosthesis for a patient with a healthy contralateral joint is provided, comprising obtaining imaging data of the patient's healthy contralateral joint surfaces, modifying the imaged data of the patient's healthy contralateral joint surfaces to provide a more functional surface topography, fabricating a replicate of the modified imaged data to provide a functional joint prosthesis.

According to another aspect of the present invention a method of manufacturing a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes, modifying the imaged data of the patient's healthy contralateral joint surfaces to provide a more functional surface topography while exhibiting the smallest deviation in overall dimensions from one of the plurality of articular joint surface archetypes, and fabricating the joint prosthesis to resemble the articular joint surface archetype which exhibits the smallest deviation in overall dimensions from the modified imaged data.

According to another aspect of the present invention an apparatus for manufacturing a joint prosthesis for a patient is provided, comprising memory means for storing a database of a plurality of joint surface archetypes acquired through measurement of a plurality of joint surfaces, said plurality of joint surface archetypes being cross-referenced by parameters including dimensions of bone associated with the joint surface, the weight of a person from whom the measurement is being taken, the sex of the person from whom the measurement is being taken, the race of the person from whom the measurement is being taken, and the height of the person from whom the measurement is being taken, input means for receiving a plurality of parameters exhibited by the patient, a microprocessor connected to said memory means for selecting one of said plurality of joint surface archetypes whose parameters most closely resemble a corresponding plurality of parameters exhibited by the patient, and a numerically-controlled fabrication means controlled by said microprocessor for fabricating the joint prosthesis to resemble the selected articular joint surface archetype.

These and other advantages will become apparent from the detailed description, accompanying the claims and attached drawing figures.

DETAILED DESCRIPTION OF THE PREFERRED EMBODIMENTS

According to one aspect of the present invention, a joint prosthesis for attachment to a bone of a patient is provided, comprising an anchor with a head surface and a stem for attachment to an end of the bone, the head surface having an anatomically accurate shape.

According to another aspect of the present invention, a total joint prosthesis for attachment to two bones of a patient is provided, comprising two unjoined anchors, each with a head surface and a stem for attachment to ends of respective ones of the two bones, each of the head surfaces having an anatomically accurate shape.

A shape of the head surface of a first one of the two anchors may be substantially identical to a metacarpal joint surface and a shape of the head surface of a second one of the two anchors may be substantially identical to a trapezial joint surface.

The stem of the first one of the two anchors may be adapted to fit within a canal in a metacarpal bone and the stem of the second one of the two anchors may be adapted to fit within a canal in a trapezial bone.

The stems may be coated with a porous metal forming a porous metal surface to promote a functional stress transfer between the bones and the stems. The porous metal surface may be formed of sintered metal. The stems may be coated with an osteogenic material forming an osteogenic surface to promote a functional stress transfer between the bones and the stems. The osteogenic surface may be formed of hydroxyapatite.

According to another aspect of the present invention, a total joint prosthesis for attachment in the bones of a patient is provided, comprising two unjoined anchors, each with a head surface and a stem for attachment to end of respective ones of the two bones, each of the head surfaces having an anatomically accurate shape based upon a particular one of a plurality of articular joint surfaces within a database of mathematical descriptions of said plurality of articular joint surfaces.

The database may comprise a plurality of articular joint surface archetypes. The articular joint surface archetypes may be cross-referenced by a plurality of anatomical parameters representing variations in anatomic form based upon race, gender, joint size, bone density, cortical thickness, and medullary cavity. Each of said articular joint surface archetypes may be derived from mathematical descriptions using spline surfaces which accurately reproduce respective anatomic human joint surface shapes. The database may be derived from experimental measurements of human joint surfaces. The experimental measurements may comprise obtaining imaging data of a plurality of human joints.

The stems may be adapted to be press-fit into respective ones of a plurality of medullary canals in the patient's bones. The stems may have a fluted surface to facilitate cement fixation in respective ones of a plurality of medullary canals in the patient's bones. The anchors may be made of biocompatible materials.

According to another aspect of the present invention a method of manufacturing a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes to determine which one of the plurality of articular joint surface archetypes exhibits the smallest deviation in overall dimensions from the imaged data, and fabricating the joint prosthesis to resemble the articular joint surface archetype which exhibits the smallest deviation in overall dimensions from the imaged data.

The step of fabricating may further comprise the step of combining a plurality of modular head and stem sections. The step of obtaining imaging data of the patient's healthy contralateral joint surfaces may comprise magnetic resonance imaging. The step of obtaining imaging data of the patient's healthy contralateral joint surfaces may comprise computed tomography.

According to another aspect of the present invention a method of selecting, from a collection, a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes to determine which one of the plurality of articular joint surface archetypes exhibits the smallest deviation in overall dimensions from the imaged data, and selecting, from the collection, the joint prosthesis which exhibits the smallest deviation in overall dimensions from the articular joint surface archetype which exhibits the smallest deviation in overall dimensions from the imaged data.

The step of selecting may further comprise the step of selecting a plurality of modular head and stem sections. The step of obtaining imaging data of the patient's healthy contralateral joint surfaces may further comprise magnetic resonance imaging. The step of obtaining imaging data of the patient's healthy contralateral joint surfaces may comprise computed tomography.

According to another aspect of the present invention a method of manufacturing a joint prosthesis for a patient with a healthy contralateral joint is provided, comprising obtaining imaging data of the patient's healthy contralateral joint surfaces, fabricating a mirror image replicate of the patient's imaged healthy contralateral joint surfaces.

The step of fabricating may further comprise the step of combining a plurality of modular head and stem sections.

The step of obtaining imaging data of the patient's healthy contralateral joint surfaces may comprise magnetic resonance imaging. The step of obtaining imaging data of the patient's healthy contralateral joint surfaces may comprise computed tomography.

According to another aspect of the present invention a method of manufacturing a joint prosthesis for a patient's bone is provided, comprising measuring a plurality of parameters including dimensions of the bone, the patient's weight, the patient's sex, and the patient's height, comparing the plurality of measured parameters with a respective plurality of corresponding parameters in a database of mathematical descriptions of a plurality of articular joint surface archetypes to determine which one of the plurality of articular joint surface archetypes has parameters exhibiting the most similarity to the measured parameters, and fabricating the joint prosthesis to resemble the articular joint surface archetype which has parameters exhibiting the most similarity to the measured parameters.

The step of fabricating may further comprise the step of combining a plurality of modular head and stem sections.

According to another aspect of the present invention a method of manufacturing a joint prosthesis for a patient's bone is provided, comprising obtaining imaging data of the joint surface of the patient's bone, modifying the imaged data of the joint surface of the patient's bone to provide a more functional surface topography, fabricating a replicate of the modified imaged data to provide a functional joint prosthesis.

The step of fabricating may further comprise the step of combining a plurality of modular head and stem sections.

The step of obtaining imaging data of the joint surface of the patient's bone may comprise magnetic resonance imaging. The step of obtaining imaging data of the joint surface of the patient's bone may comprise computed tomography.

According to another aspect of the present invention a method of manufacturing a joint prosthesis for a patient's bone is provided, comprising obtaining imaging data of the joint surface of the patient's bone, comparing the imaged data of the joint surface of the patient's bone with a database of mathematical descriptions of a plurality of articular joint surface archetypes, modifying the imaged data of the joint surface of the patient's bone to provide a more functional surface topography while exhibiting the smallest deviation in overall dimensions from one of the plurality of articular joint surface archetypes, fabricating the joint prosthesis to resemble the articular joint surface archetype which exhibits the smallest deviation in overall dimensions from the modified imaged data.

The step of fabricating may further comprise the step of combining a plurality of modular head and stem sections.

The step of obtaining imaging data of the joint surface of the patient's bone may comprise magnetic resonance imaging. The step of obtaining imaging data of the joint surface of the patient's bone may comprise computed tomography.

According to another aspect of the present invention a method of manufacturing a joint prosthesis for a patient with a healthy contralateral joint is provided, comprising obtaining imaging data of the patient's healthy contralateral joint surfaces, modifying the imaged data of the patient's healthy contralateral joint surfaces to provide a more functional surface topography, fabricating a replicate of the modified imaged data to provide a functional joint prosthesis.

The step of fabricating may further comprise the step of combining a plurality of modular head and stem sections.

The step of obtaining imaging data of the patient's healthy contralateral joint surfaces may comprise magnetic resonance imaging. The step of obtaining imaging data of the patient's healthy contralateral joint surfaces may comprise computed tomography.

According to another aspect of the present invention a method of manufacturing a joint prosthesis for a patient with a healthy contralateral joint is provided, comprising obtaining imaging data of the patient's healthy contralateral joint surfaces, comparing the imaged data of the patient's healthy contralateral joint surfaces with a database of mathematical descriptions of a plurality of articular joint surface archetypes, modifying the imaged data of the patient's healthy contralateral joint surfaces to provide a more functional surface topography while exhibiting the smallest deviation in overall dimensions from one of the plurality of articular joint surface archetypes, and fabricating the joint prosthesis to resemble the articular joint surface archetype which exhibits the smallest deviation in overall dimensions from the modified imaged data.

The step of fabricating may further comprise the step of combining a plurality of modular head and stem sections.

The step of obtaining imaging data of the patient's healthy contralateral joint surfaces may comprise magnetic resonance imaging. The step of obtaining imaging data of the patient's healthy contralateral joint surfaces may comprise computed tomography.

According to another aspect of the present invention an apparatus for manufacturing a joint prosthesis for a patient is provided, comprising memory means for storing a database of a plurality of joint surface archetypes acquired through measurement of a plurality of joint surfaces, said plurality of joint surface archetypes being cross-referenced by parameters including dimensions of bone associated with the joint surface, the weight of a person from whom the measurement is being taken, the sex of the person from whom the measurement is being taken, the race of the person from whom the measurement is being taken, and the height of the person from whom the measurement is being taken, input means for receiving a plurality of parameters exhibited by the patient, a microprocessor connected to said memory means for selecting one of said plurality of joint surface archetypes whose parameters most closely resemble a corresponding plurality of parameters exhibited by the patient, and a numerically-controlled fabrication means controlled by said microprocessor for fabricating the joint prosthesis to resemble the selected articular joint surface archetype.

Figure 1:
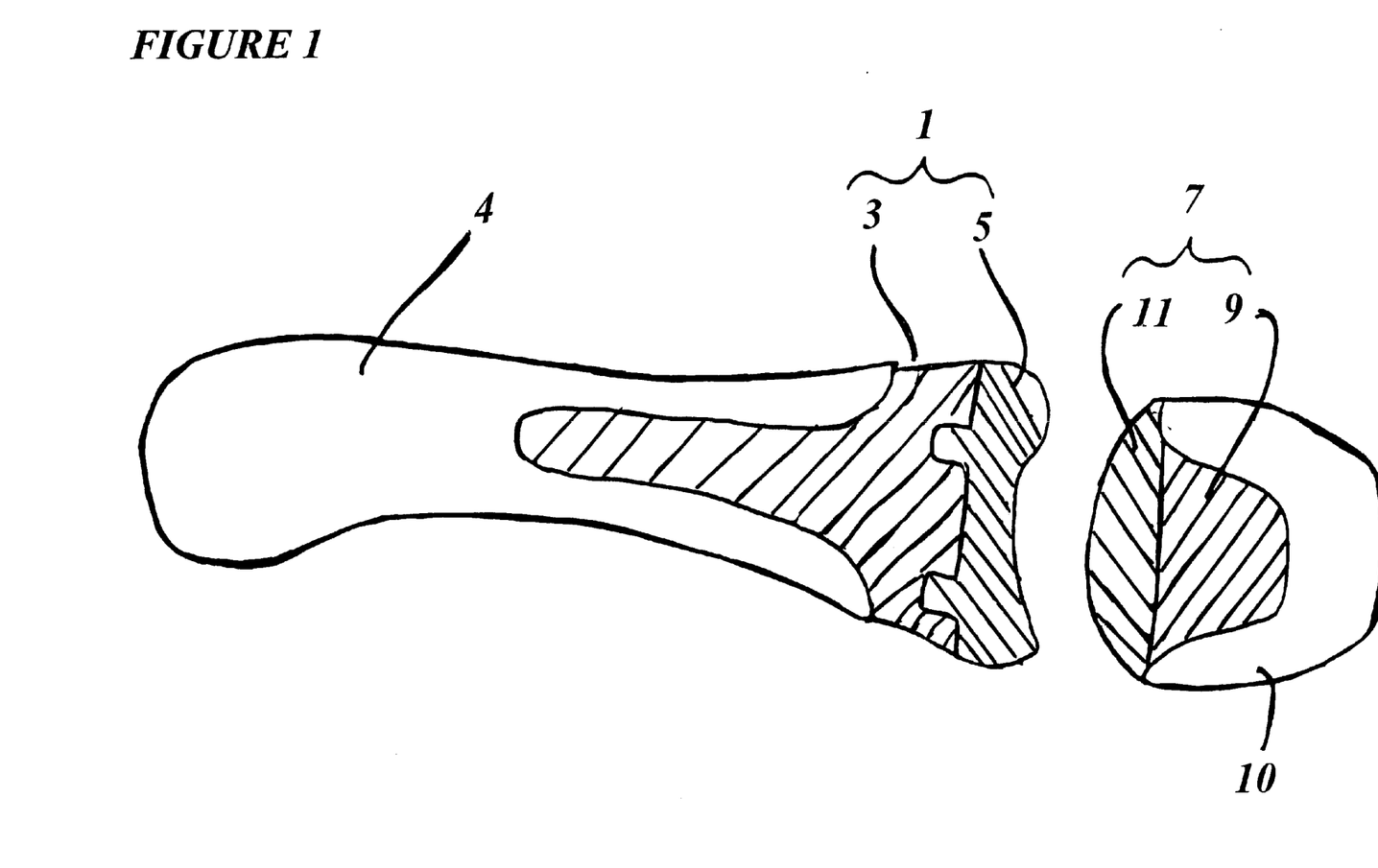
FIG. 1 shows the construction of a first embodiment of the present invention.

Referring now to the FIGS., FIG. 1 shows a total joint prosthesis according to a first embodiment of the present invention, which results from the method of the present invention. The invention is particularly suited for use in the metacarpal and trapezial bones. The preferred embodiment will be described with reference to the metacarpal and trapezial bones, but this is by way of example, and not limitation, as the present invention may also be used to replace the proximal interphalangeal joint as well as well as other joints in the body.

A first embodiment of the invention comprises a first anchor 1 including metacarpal stem 3 for insertion into a canal in the metacarpal bone 4 and a metacarpal head 5. A second anchor 7 incudes trapezial stem 9 for insertion into a canal in the trapezial bone 10 and trapezial head 11. This embodiment results is a total joint prosthesis.

Figure 2:
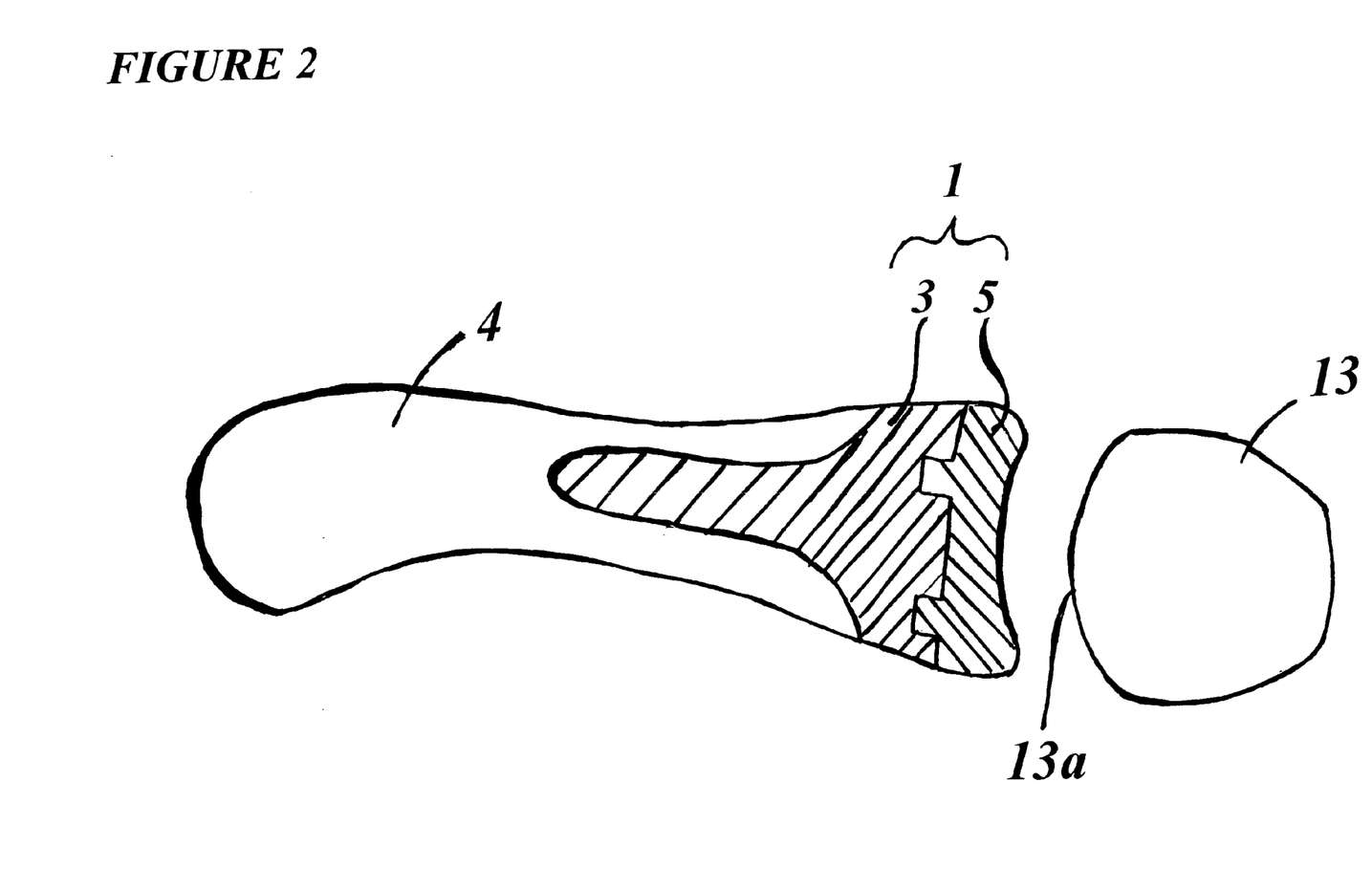
FIG. 2 shows the construction of a second embodiment of the present invention.

A second embodiment of the present invention is shown in FIG. 2, wherein the same reference numerals of FIG. 1 are applied to the same parts and therefore do not require detailed description. This second embodiment results in a partial joint prosthesis, in which only one of the joint surfaces is replaced by the prosthesis of the instant invention. As seen in this FIG., the first anchor 1, includes metacarpal stem 3 for insertion into a canal in the metacarpal bone 4 and a metacarpal head 5 slidably contacts the joint surface 13a of the trapezial bone 13.

Figure 3:
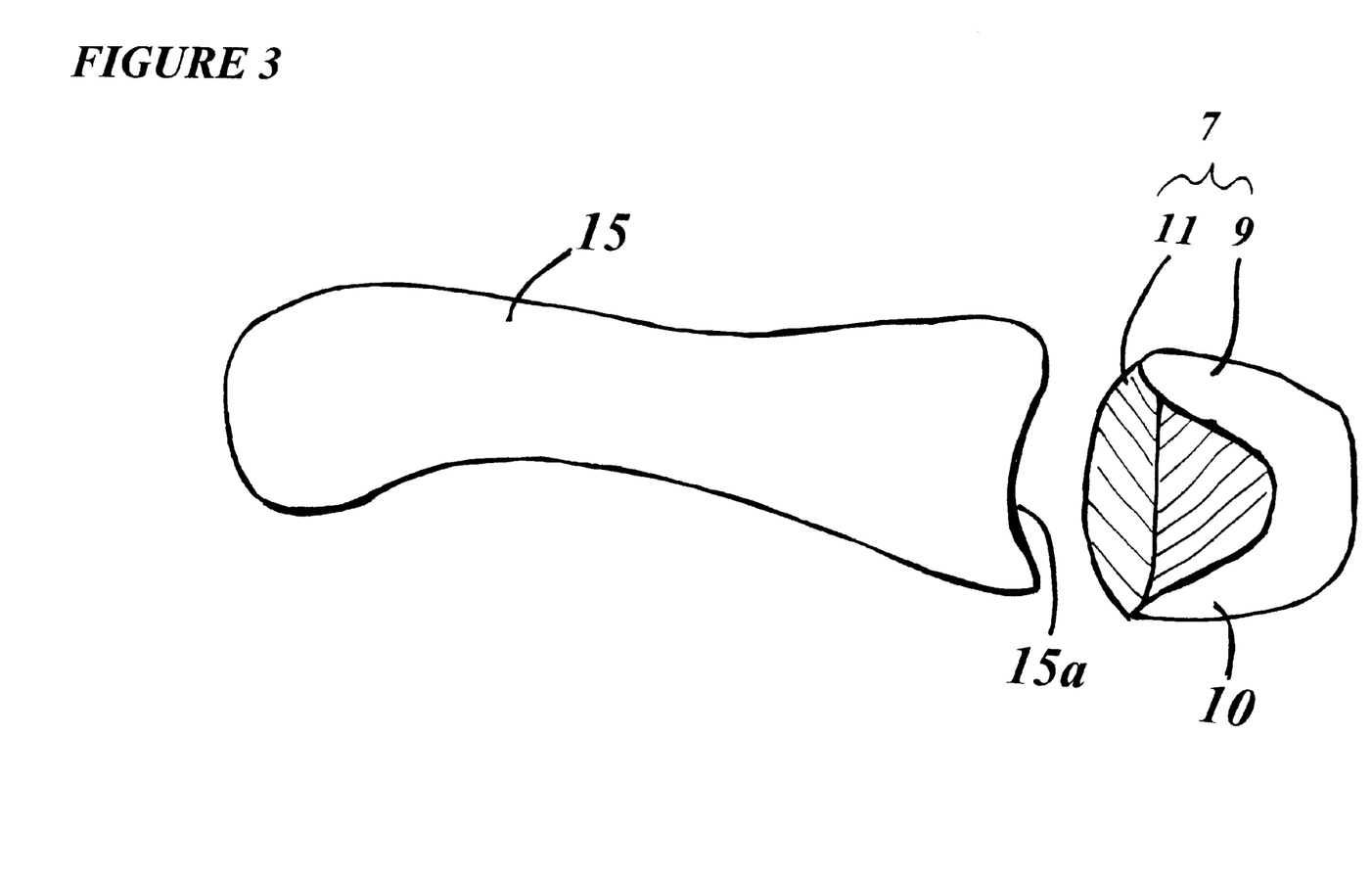
FIG. 3 shows the construction of a third embodiment of the present invention.

A third embodiment of the present invention is shown in FIG. 3, wherein the same reference numerals of FIG. 1 are applied to the same parts and therefore do not require detailed description. This third embodiment results in a partial joint prosthesis, in which only one of the joint surfaces is replaced by the prosthesis of the instant invention. As seen in this FIG., the second anchor 7 incudes trapezial stem 9 for insertion into a canal in the trapezial bone 10 and trapezial head 11. The trapezial head 11 slidably contacts the joint surface 15a of the metacarpal bone 15.

The apparatus of the instant invention may be made by a first method of the instant invention in which a patient has one joint which needs replacement and one healthy contralateral joint. In this method, imaging data of the patient's healthy contralateral joint surfaces is taken and the imaged data is compared to a database of mathematical descriptions of a plurality of articular joint surface archetypes to determine which one of the plurality of articular joint surface archetypes exhibits the smallest deviation in overall dimensions from the imaged data. Each articular joint surface archetype is a set of data that represents a different joint surface topography.

Once the comparison is done to determine which one of the plurality of articular joint surface archetypes exhibits the smallest deviation in overall dimensions from the imaged data, a joint prosthesis resembling that archetype is fabricated. Alternatively, prosthesis components modeled after some or all of the archetypes may be kept on hand and a best-fit prosthesis may be utilized.

Another method according to the instant invention that produces the prosthesis of the instant invention is similar to the first method but does not rely on imaged data from a healthy contralateral joint of the patient. In this method, a plurality of parameters including dimensions of the bone to receive the prosthesis, the patent's weight, the patent's height and the patient's sex are compared to a respective plurality of corresponding parameters in the database of mathematical descriptions of joint surface archetypes to determine which one of the archetypes has parameters exhibiting the most similarity to the measured parameters. Once the archetype with parameters exhibiting the most similarity to the measured parameters is chosen, the prosthesis is then fabricated in the same manner as in the first method.

A third method that produces the prosthesis of the instant invention involves obtaining imaging data from a healthy contralateral joint and then permits modification of the imaged to provide a more functional joint topography before the modified imaged data is utilized as a model for the fabrication of the prosthesis.

Figure 4:
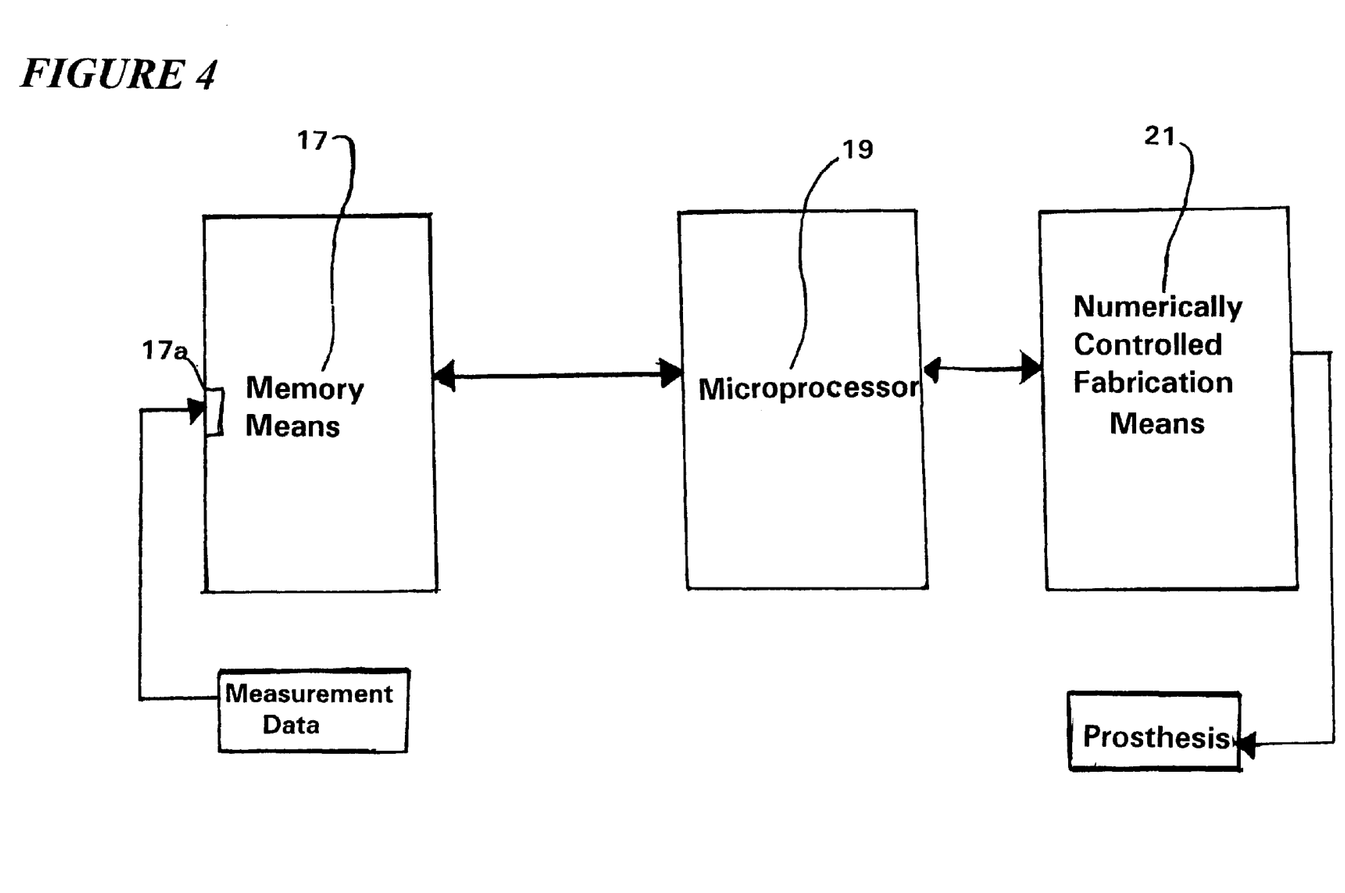
FIG. 4 shows the construction of an embodiment of an apparatus according to the present invention for making a joint prosthesis according to a method of the present invention.

An apparatus that may be used to produce the joint prosthesis of the present invention according to the method of the present invention is shown in FIG. 4. In this FIG, it is seen that a memory means 17 is used for storing a database of a plurality of joint surface archetypes acquired through measurement of a plurality of joint surfaces of different people. The database is input to the memory means through input port 17a. The plurality of joint surface archetypes are cross-referenced by parameters including dimensions of bone associated with the joint surface, the weight of the person from whom the joint measurements were taken, the sex of that person, and the height of that person.

A microprocessor 19 is connected to the memory means 17 for selecting one of the plurality of joint surface archetypes whose parameters most closely resemble a corresponding plurality of parameters exhibited by the patient. A numerically-controlled fabrication means 21 is controlled by the microprocessor 19 for fabricating the joint prosthesis to resemble the selected articular joint surface archetype.

The database may store the joint surface archetype information as, for example, a plurality of coordinates, as a spline function, or as a series of coefficients of a spline function.

Further the database of articular joint surface archetypes may be cross-referenced by a plurality of anatomical parameters representing variations in anatomic form based upon gender, joint size, bone density, cortical thickness, and medullary cavity.

In addition, as known by one skilled in the art, and as described in references (2) and (3), a single parametric biquintic spline function can describe an articular surface.

That is, the general form of a bivariate parametric polynomial surface of degree n is given by $$x_k(u, w) = \sum_{i=0}^{n} \sum_{j=0}^{n} a_{ijk} u^i w^j \qquad (1)$$

where $x_k$ represents a point on the surface at the parametric coordinates (u, w), k=1,2,3 indicates the three coordinate directions and $a_{ijk}$ (i, j=0 to n) represents the polynomial coefficients of u and w. In order to fit such an equation to experimental data, each experimental point $P^v_k$ is assigned a set of parametric coordinates ($u_v$, $W_v$), where v varies from 1 to N, the total number of data points. These parametric coordinates are assigned as follows. When a grid is projected on the joint surface, the left most column and the lowest row of the grid which appear on the surface are denoted as column 1 and row 1, respectively. Similarly, the last column and the last row are denoted as column $n_c$ and row $n_r$. A data point which represents the intersection of row r and column c ($1 \leq r \leq n_r$; $1 \leq c \leq n_c$) is assigned the parametric coordinates u=(c−1)/$n_c$−1) and w=(r−1)/($n_r$−1). Thus, the parametric coordinates (u,w) vary from zero to one.

To determine the coefficients $a_{ijk}$ of the surface using a least-squares analysis, the objective functions $f_k$ (k=1,2,3) in $$f_k = \sum_{v=1}^{N} \sum_{l=0}^{n} \sum_{m=0}^{n} (a_{lmk} u^l w^m - p_k^v)^2 \qquad (2)$$

are minimized. The extremum value of $f_k$ is obtained by setting $f_k/a_{ijk}$=0, which results in the following expression:

$$\sum_{v=1}^{N} \sum_{l=0}^{n} \sum_{m=0}^{n} a_{lmk} u^{i+l} w^{j+m} = \sum_{v=1}^{N} p_k^v u_v^i w_v^j \qquad (3)$$

Equation (3) represents three independent linear systems (k=1,2,3) in the unknowns $a_{lmk}$. As i and j are varied from 0 to n, equation (3) yields a set of $(n+1)^2$ equations with an equal number of unknowns. In a practical application, equation (3) should be converted to the usual form for linear systems, e.g. $Ay_k=b_k$, where $y_k$ is the vector containing the unknowns (i,j=0 to n). This system can be solved if there are at least $(n+1)^2$ data points on the surface, using any suitable algorithm for systems of linear equations. Note that the coefficients of a, on the left-hand side of equation (3) or, equivalently, the elements of matrix A, need only be evaluated once since they do not depend on k.

The global root-mean-square error of the surface-fitting procedure, which combines the error at the surface nodal points in all three coordinate directions, is given by $$e = \frac{f_1 + f_2 + f_3}{N}. \qquad (4)$$

The degree n of the surface which best fits the experimental data is chosen such as to minimize this surface fitting error e.

Therefore, each archetype may be derived from mathematical descriptions using spline surfaces which reproduce the anatomic shape of each head surface.

The experimental data utilized to compile the database of archetypes may be gathered through various methods, such as magnetic resonance imaging, computed tomography, or stereophotogrammetry, such as in (1), (2), and (3).

Stereophotogrammetry (SPG), for example, is a technique used to obtain precise three-dimensional measurements of an object through the process of recording and measuring two-dimensional photographic images, combined with appropriate mathematical computations using both perspective and projective geometry. From the SPG technique, a three-dimensional mathematical model may be constructed based on information obtained from digitized points on two two-dimensional photographs of the object surface. The SPG technique may be specifically designed for diarthrodial joint studies and may be capable of measuring cartilage and underlying bone surface topography, surface areas, and cartilage thickness. The SPG technique may be used to determine anatomic quantities for the human distal femur, retropatellar surface, menisci, and tibial plateau, for example.

Figure 5:
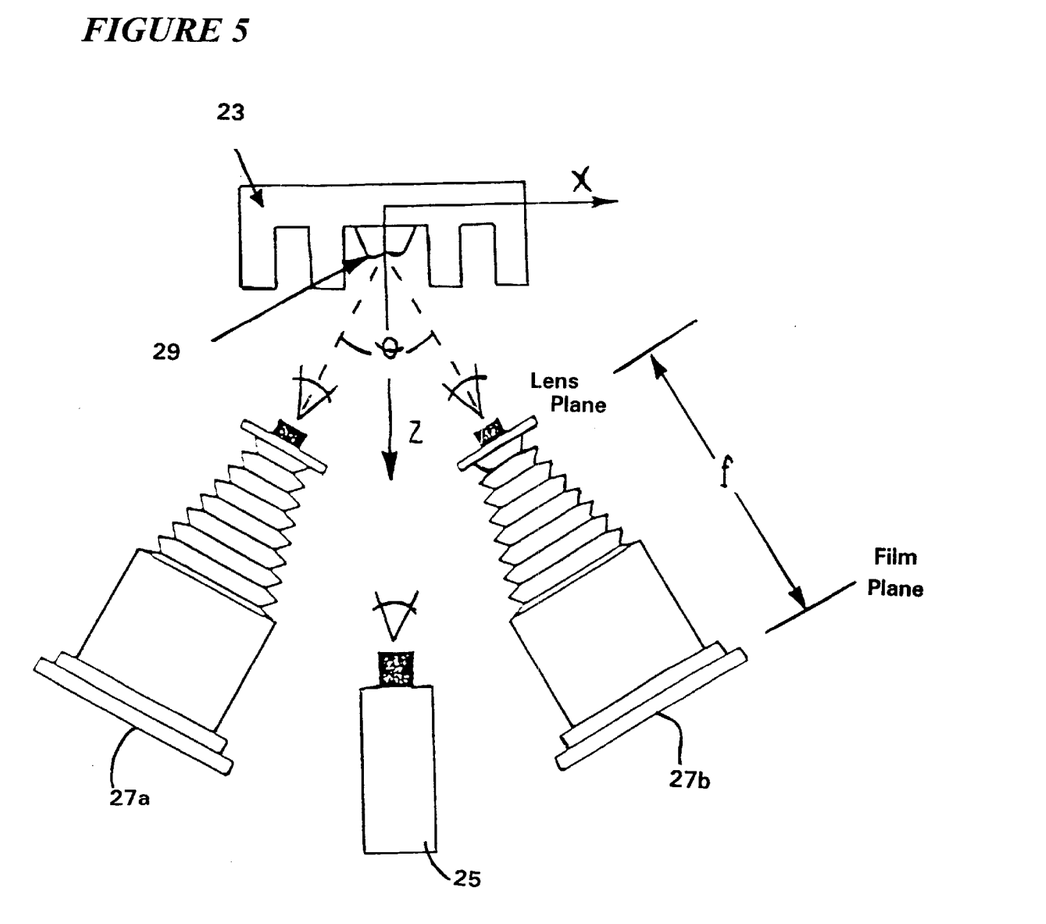
FIG. 5 shows the construction of a data acquisition apparatus utilized to make a joint prosthesis according to a method of the present invention.

An SPG apparatus may consist of several components necessary for data acquisition, as seen in FIG. 5. These components may include a calibration frame and a specimen mounting system 23, a high intensity optical spotlight 25, two precision large format cameras 27(a) and (b), a film processor (not shown), an X-Y coordinate digitizer with video camera and monitor (not shown), and supporting computer facilities (not shown). The specimen is depicted as element 29.

Two precision calibration frames of different dimensions may be used for a wide range of joint sizes. The larger frame may have outer dimensions of 24.4×20.3×5.1 cm with a working space of 12.7×12.7×5.1 cm, large enough to accommodate any diarthrodial joint surface in the human body. The smaller frame may have outer dimensions of 12.2× 10.2×2.5 cm, and a working space of 6.4×6.4×2.5 cm, which may be used for smaller joints such as those of the hand. The frames may be made from a reaction-bonded silicon nitride ceramic material ($Si_3N_4$) which has a significantly lower coefficient of thermal expansion than steel or aluminum. Sixteen optical targets may be affixed to each frame to serve as control points for the stereophotogrammetric procedure. These targets may be made of a white opaque film, and may consist of a black crossline surrounded by concentric circles used for optical alignment (line width may equal 100 $\mu$m for the small frame).

After disarticulation and removal of the surrounding soft tissue, the joint surfaces may be positioned within the calibration frame using a specimen mounting system. This system may consist of a disposable Plexiglas specimen plate to which the specimen is rigidly fixed using a cancellous screw and cyanoacrylate cement. This specimen plate may be rigidly fixed to an inner alignment frame. Optical alignment targets, of the type described above, may be affixed to 12 Acetal round rods of various lengths (1–5 cm) which are rigidly mounted on the alignment frame. These alignment targets and rods are distributed in a non-uniform fashion around the periphery of the specimen on the alignment frame. During photography, the specimen, fixed to the alignment frame, is inserted into the calibration frame. The entire assembly may be supported on an aluminum base resting on vibration pads.

A high intensity optical spotlight, equipped with an F2.8 70–125 mm zoom lens and a flash tube rated at 1200 W·s, may be utilized to project a fine grid pattern on the joint surface. These grid intersections serve as recognizable target points (nodes) on the joint surface which will be digitized from photographs. The grid pattern may be produced with a line width of 12.5 $\mu$m and line spacing of 72.5 $\mu$m, and may be projected from a 35 $\mu$m glass slide. When projected on the joint surface, the line width varies from 50–150 $\mu$m with line spacing of approximately 0.7–2.3 mm depending on the size and curvature of the joint surface under consideration.

The frames and specimen may be photographed from two camera positions separated by a collimation angle $\theta$ of approximately 40° using two 20×25 cm (8×10 in) format cameras equipped with high quality F9 240 mm lenses set at F90 to provide the necessary depth of field. Black and white 20×25 cm (8×10 in) Polaroid print film may be used in the cameras and may be processed in the laboratory. Calibration targets, alignment targets, and grid intersections appearing in each stereogram (the pair of photographs) may be digitized using the Aristocrat 102D X-Y digitizer which has a resolution of 5 $\mu$m and a rated accuracy of 20 $\mu$m. The digitizer consists of a 86×86 cm working table, an expansion module with a serial port for on-line connection to a host computer, and a closed-circuit television system. An interactive graphics program displays the digitized points during data acquisition and saves their coordinates in a computer file. Digitizing time for an experienced operator varies from 2 to 4 h for an average size joint surface.

For quantifying the underlying bone surface of the joint and measuring the cartilage thickness, the specimen and alignment frame may be removed from the calibration frame after being photographed, and may be carefully submerged in a solution of 5.25% sodium hypochlorite. This solution gently dissolves the cartilage layer over a period of 3–6 h down to the level of the tidemark. This surface may then be carefully sprayed with a thin layer of white paint (measured to be <15 $\mu$m) to improve grid contrast. The specimen and alignment frame are subsequently repositioned inside the calibration frame and the bone surface is photographed and digitized using the same procedure as for the cartilage surface. The alignment targets, which do not move relative to the bone substrate of the specimen, are used to realign the bone and cartilage surfaces into a common frame of reference.

It must be noted that although the present invention is described by reference to particular embodiments thereof, many changes and modifications of the invention may become apparent to those skilled in the art without departing from the spirit and scope of the invention as set forth in the claims.

REFERENCES

1. G. A. Ateshian, L. J. Solsowsky, and V. C. Mow, *Quantitation of Articular Surface Topography and Cartilage Thickness in Knee Joints Using Stereophotogrammetry*, J. Biomechanics, Vol. 24. No. 8, pp. 761–776, 1991.
2. G. A. Ateshian, M. P. Rosenwasser, and V. C. Mow, *Curvature Characteristics and Congruence of the Thumb Carpometacarpal Joint: Differences Between Female and Male Joints*, J. Biomechanics, Vol. 25, No. 6, pp. 591–607, 1992.
3. G. A. Ateshian, *A Least-Squares B-Spline Surface-Fitting Method For Articular Surfaces Of Diarthrodial Joints*, J. Biomech. Engng, ASME, Vol. 115, pp.366–373.

What is claimed is:

1. A method of manufacturing a joint prosthesis to replace a joint for a patient with a healthy joint contralateral to the joint to be replaced, comprising:
   obtaining imaging data of the patient's healthy contralateral joint surfaces;
   comparing the imaged data of the patient's healthy contralateral joint surfaces with a database of mathematical descriptions of a plurality of articular joint surface archetypes to determine which bone of the plurality of articular joint surface archetypes exhibits the smallest deviation in overall dimensions from the imaged data; and
   fabricating, for the joint to be replaced, a joint prosthesis to resemble the mirror image of the articular joint surface archetype which exhibits the smallest deviation in overall from the imaged data.

2. The method of claim 1, wherein the step of fabricating further comprises the step of combining a plurality of modular head and stem sections.

3. The method of claim 1, wherein the step of obtaining imaging data of the patient's healthy contralateral joint surfaces comprises magnetic resonance imaging.

4. The method of claim 1, wherein the step of obtaining imaging data of the patient's healthy contralateral joint surfaces comprises computed tomography.

5. A method of selecting, from a collection, a joint prosthesis to replace a joint for a patient with a healthy joint contralateral to the joint to be replaced, comprising:
   obtaining imaging data of the patient's healthy contralateral joint surfaces of the healthy joint contralateral to the joint to be replaced;
   comparing the imaged data of the patient's healthy contralateral joint surfaces with a database of mathematical descriptions of a plurality of articular joint surface archetypes to determine which one of the plurality of articular joint surface archetypes exhibits the smallest deviation in overall dimensions from the imaged data; and
   selecting, from the collection, for the joint to be replaced, the joint prosthesis which exhibits the smallest deviation in overall dimensions from the mirror image of the articular joint surface archetype which exhibits the smallest deviation in overall dimensions from the imaged data.

6. The method of claim 5, wherein the step of selecting further comprises the step of selecting a plurality of modular head and stem sections.

7. The method of claim 5, wherein the step of obtaining imaging data of the patient's healthy contralateral joint surfaces comprises magnetic resonance imaging.

8. The method of claim 5, wherein the step of obtaining imaging data of the patient's healthy contralateral joint surfaces comprises computed tomography.

9. A method of manufacturing a joint prosthesis to replace a joint for a patient with a healthy joint contralateral to the joint to be replaced, comprising:
   obtaining imaging data of the patient's healthy contralateral joint surfaces;
   fabricating, for the joint to be replaced, a mirror image replicate of the patient's imaged healthy contralateral joint surfaces.

10. The method of claim 9, wherein the step of fabricating further comprises the step of combining a plurality of modular head and stem sections.

11. The method of claim 9, wherein the step of obtaining imaging data of the patient's healthy contralateral joint surfaces comprises magnetic resonance imaging.

12. The method of claim 9, wherein the step of obtaining imaging data of the patient's healthy contralateral joint surfaces comprises computed tomography.

13. A method of manufacturing a joint prosthesis for a patient's bone, comprising:
   measuring a plurality of parameters including dimensions of the bone, the patient's weight, the patient's sex, and the patient's height;
   comparing the plurality of measured parameters with a respective plurality of corresponding parameters in a database of mathematical descriptions of a plurality of articular joint surface archetypes to determine which one of the plurality of articular joint surface archetypes has parameters exhibiting the most similarity to the measured parameters; and
   fabricating the joint prosthesis to resemble the articular joint surface archetype which has parameters exhibiting the most similarity to the measured parameters.

14. The method of claim 13, wherein the step of fabricating further comprises the step of combining a plurality of modular head and stem sections.

15. A method of manufacturing a joint prothesis for a patient's bone, comprising:
   obtaining imaging data of the joint surface of the joint contralateral to the patient's bone for which the joint prosthesis is being made;
   modifying the imaged data of the joint surface of the joint contralateral to the patient's bone to provide a more functional surface topography; and
   fabricating a mirror image replicate of the modified imaged data to provide a functional joint prosthesis.

16. The method of claim 15, wherein the step of fabricating further comprises the step of combining a plurality of modular head and stem sections.

17. The method of claim 15, wherein the step of obtaining imaging data of the joint surface of the patient's bone comprises magnetic resonance imaging.

18. The method of claim 15, wherein the step of obtaining imaging data of the joint surface of the patient's bone comprises computed tomography.

19. A method of manufacturing a joint prosthesis for a patient's bone, comprising:
   obtaining imaging data of the joint surface of the joint contralateral to the patiently bone for which the joint prosthesis is being made;
   comparing the imaged data of the joint surface of the patient's bone with a database of mathematical descriptions of a plurality of articular joint surface archetypes;
   modifying the imaged data of the joint surface of the joint contralateral to the patient's bone to provide a more functional surface. topography while exhibiting the smallest deviation in overall dimensions from one of the plurality of articular joint surface archetypes;

fabricating the joint prosthesis to resemble the articular joint surface archetype which exhibits the smallest. deviation in overall dimensions from the Mirror image of the modified imaged data.

20. The method of claim 19, wherein the step of fabricating further comprises the step of combining a plurality of modular head and stem sections.

21. The method of claim 19, wherein the step of obtaining imaging data of the joint surface of the patient's bone comprises magnetic resonance imaging.

22. The method of claim 19, wherein the step of obtaining imaging data of the joint surface of the patient's bone comprises computed tomography.

23. A method of manufacturing a joint prosthesis to replace a joint for a patient with a healthy joint contralateral to the joint to be replaced, comprising:

obtaining imaging data of the patient's healthy contralateral joint surfaces;

modifying the imaged data of the patient's healthy contralateral joint surfaces to provide a more functional surface topography;

fabricating a replicate joint prosthesis of the mirror image of the modified imaged data to provide a functional joint prosthesis.

24. The method of claim 23, wherein the step of fabricating further comprises the step of combining a plurality of modular head and stem sections.

25. The method of claim 23, wherein the step of obtaining imaging data of the patient's healthy contralateral joint surfaces comprises magnetic resonance imaging.

26. The method of claim 23, wherein the step of obtaining imaging data of the patient's healthy contralateral joint surfaces comprises computed tomography.

27. A method of manufacturing a joint prosthesis to replace a joint for a patient with a healthy joint contralateral to the joint to be replaced, comprising:

obtaining imaging data of the patient's healthy contralateral joint surfaces;

comparing the imaged data of the patient's healthy contralateral joint surfaces with a database of mathematical descriptions of a plurality of articular joint surface archetypes;

modifying the imaged data of the patient's healthy contralateral joint surfaces to provide a more functional surface topography while exhibiting the smallest deviation in overall dimensions from one of the plurality of articular joint surface archetypes; and fabricating the joint prosthesis to resemble the mirror image of the articular joint surface archetype which provides a functional joint prosthesis which also exhibits the smallest deviation in overall dimensions from the modified imaged data.

28. The method of claim 27, wherein the step of fabricating further comprises the step of combining a plurality of modular head and stem sections.

29. The method of claim 27, wherein the step of obtaining imaging data of the patient's healthy contralateral joint surfaces comprises magnetic resonance imaging.

30. The method of claim 27, wherein the step of obtaining imaging data of the patient's healthy contralateral joint surfaces comprises computed tomography.

31. An apparatus for manufacturing a joint prosthesis for a patient, comprising:

memory means for storing a database of a plurality of joint surface archetypes acquired through measurement of a plurality of joint surfaces, said plurality of joint surface archetypes being cross-referenced by parameters including dimensions of bone associated with the joint surface, the weight of a person from whom the measurement is being taken, the sex of the person from whom the measurement is being taken, the race of the person from whom the measurement is being taken, and the height of the person from whom the measurement is being taken;

input means for receiving a plurality of parameters exhibited by the patient;

a microprocessor connected to said memory means for selecting one of said plurality of joint surface archetypes whose parameters most closely resemble a corresponding plurality of parameters exhibited by the patient; and a numerically-controlled fabrication means controlled by said microprocessor for fabricating the joint prosthesis to resemble the selected articular joint surface archetype.

* * * * *